United States Patent
Gu (10) Patent No.: US 11,291,591 B1
(45) Date of Patent: Apr. 5, 2022

(54) SMART MONITORING SYSTEM WITH WETNESS DETECTION

(71) Applicant: VestConn Inc., Lexington, MA (US)

(72) Inventor: Lei Gu, Lexington, MA (US)

(73) Assignee: VestConn Inc., Lexington, MA (US)

(*) Notice: Subject to any disclaimer, the term of this patent is extended or adjusted under 35 U.S.C. 154(b) by 0 days.

(21) Appl. No.: 17/340,821

(22) Filed: Jun. 7, 2021

Related U.S. Application Data (60) Provisional application No. 63/094,846, filed on Oct. 21, 2020, provisional application No. 63/080,440, filed on Sep. 18, 2020.

(51) Int. Cl.
| | | |
|---|---|---|
| A61F 13/42 | (2006.01) |
| A61F 13/84 | (2006.01) |
| A61F 13/49 | (2006.01) |
| B33Y 80/00 | (2015.01) |

(52) U.S. Cl.
CPC .............. *A61F 13/42* (2013.01); *A61F 13/49* (2013.01); *A61F 13/84* (2013.01); *B33Y 80/00* (2014.12); *A61F 2013/424* (2013.01); *A61F 2013/426* (2013.01); *A61F 2013/8473* (2013.01)

(58) Field of Classification Search
CPC .......... A61F 13/42; A61F 13/49; A61F 13/84; A61F 2013/424; A61F 2013/426; A61F 2013/8473
See application file for complete search history.

(56) References Cited

U.S. PATENT DOCUMENTS

| | | |
|---|---|---|
| 6,603,403 B2 | 8/2003 | Jeutter et al. |
| 8,471,715 B2 | 6/2013 | Solazzo et al. |
| 8,698,641 B2 | 4/2014 | Abraham et al. |
| 8,866,624 B2 | 10/2014 | Ales, III et al. |
| 8,975,465 B2 | 3/2015 | Hong et al. |
| 9,675,497 B1 | 6/2017 | Levin |
| 9,724,247 B2 | 8/2017 | Thoen |
| 10,271,998 B2 | 4/2019 | LaVon et al. |
| 10,292,112 B2 | 5/2019 | LaVon et al. |
| 2013/0018340 A1 | 1/2013 | Abraham et al. |
| 2017/0224554 A1 | 8/2017 | LaVon et al. |
| 2019/0060137 A1* | 2/2019 | Severns .......... G06K 19/07745 |

FOREIGN PATENT DOCUMENTS

EP  2 713 973 B1  6/2016

OTHER PUBLICATIONS

International Search Report and Written Opinion for International Application No. PCT/US2021/038602, dated Oct. 1, 2021.

\* cited by examiner

*Primary Examiner* — Catharine L Anderson
(74) *Attorney, Agent, or Firm* — Wolf, Greenfield & Sacks, P.C.

(57) ABSTRACT

A smart monitor system to capture information such as a subject's breathing rate, body temperature, daily activities, and/or the status of an absorbent article. The system may alert a parent, care provider or attendant when certain parameters fall outside of a specific range. The system may comprise a housing including at least a sensor and a signal processing unit for wirelessly transmitting signals, and a flexible sensing element which may be stretchable and washable.

15 Claims, 8 Drawing Sheets

SMART MONITORING SYSTEM WITH WETNESS DETECTION

RELATED APPLICATIONS

This application claims the benefit under 35 U.S.C. § 119(e) of the filing date of commonly assigned U.S. Provisional Patent Application No. 63/094,846, filed Oct. 21, 2020, entitled "Smart Monitoring System For Detecting Diaper Wetness," and of the filing date of commonly assigned U.S. Provisional Patent Application No. 63/080,440, filed Sep. 18, 2020, entitled "Smart Monitoring System For Detecting Diaper Wetness." Each of the documents listed above is incorporated herein by reference in its entirety.

FIELD OF THE INVENTION

Embodiments of the present invention relate generally to monitoring baby activities.

BACKGROUND OF THE INVENTION

A new parent may wish to safeguard their baby's safety, health and well-being, and as such may be interested in knowing about the frequency at which the baby urinates or defecates, its breathing rate, sleeping time, sleeping quality, sleeping position, daily activities, such as rolling, crawling and/or walking. Monitors exist for watching and listening to some baby activities, but these are incapable of recognizing unsafe situations, such as when the baby may be susceptible to SIDS (Sudden Infant Death Syndrome), or if a soiled diaper needs to be changed. Existing monitors are also unable to provide statistics on a baby's activities, such as how many diapers are changed daily, the baby's sleeping pattern, how much the baby rolls over, and how far a baby crawls and walks daily.

As one example, U.S. Pat. No. 8,471,715 B2 to Solazzo et al. describes a disposable diaper with wireless alarm system. The diaper includes two conductive strips inside. The resistance between strips will change when the diaper change from dry to wet. The conductive strips are plugged into a wireless alarm system that is attachable and removable from a diaper.

U.S. Pat. No. 9,675,497 B1 to Levin describes a bed patient monitor apparatus including a base member that has a first surface and an opposite second surface. A porous sheet over the first surface is intended to contact the skin of the patient. The second surface of apparatus is intended to lie against undergarment or diaper. A moisture sensor comprises two metallic conductors and is positioned under the first surface of the base member case. The moisture sensor is configured to generate a radio signal upon the detection of moisture by the use of metallic conductors that react to increase in conductivity between the conductors due to moisture such as urine.

U.S. Pat. No. 8,975,465 B2 to Hong et al. describes a diaper having wetness detectors. The diaper includes a first set of contacts and a second set of contacts which are constituted by conductive wires. The conductive wires form a first set of contacts and a second set of contacts. When a wetness event happens, wetness detectors senses the electrical properties of the sets of contacts and outputs a signal and excretion status.

U.S. Pat. No. 8,698,641, B2 to Abraham et al. describes a body fluid discriminating sensor that can discriminate between a urine insult and a fecal insult. The body fluid discriminating sensor can be an impedance sensor adapted to monitor changes in impedance due to an insult or an electronic nose sensor configured to provide signals associated with the presence of one or more volatile organic compounds in the absorbent article. The body fluid discriminating sensor comprises a first conductive element and a second conductive element dispose in the absorbent article. Body fluid insult changes electrical property between the first conductive element and a second conductive element.

U.S. Pat. No. 9,724,247 B2 to Thoen describes a sensor for detecting one of urination and excretion into an incontinence garment. The sensor is integrated or manufacture in incontinence garments. The sensor comprises an activation unit and a sensing unit and being connectable to a power supply. The activation unit comprising at least two spaced-apart electrodes and a switch arranged in series with the sensing unit and being for connecting the sensing unit to a power supply; wherein the activation unit is configured to activate the sensing unit in the presence of moisture by closing the switch. When the incontinence garments are dry, the switch in activation is open and isolate the sensing unit from power supply for "long shelf-life". When the incontinence garments are wet, the switch in activation is closed and electrically connect the sensing unit to power supply. The incontinence garment may include a wireless transmitter for directly or indirectly alerting a care working on the occurrence of soiling the garment.

U.S. Pat. No. 8,866,624 B2 to Ales et al. describes a conductor-less detection system for an absorbent article that indicates a change in an absorbent article such as presence of a body fluid. The various signaling systems do not include any conductive elements contained on the interior of the article. A signaling device comprises a housing and a capacitive sensor disposed within the housing. The capacitive sensor is adapted to sense a change in capacitance due to an insult to the absorbent article. The signaling device can include an attachment mechanism for removably attaching the housing to the absorbent article.

SUMMARY OF THE INVENTION

Some embodiments of the invention are directed to an apparatus for sensing presence of liquid in an absorbent article adapted to be worn by a wearer. The absorbent article has a first, inwardly-facing exterior surface and a second, outwardly-facing exterior surface. The first, inwardly-facing exterior surface resides, when the absorbent article is worn by the wearer, closer to the wearer than the second, outwardly-facing exterior surface, the apparatus comprises: a plurality of sensing elements for detecting presence of liquid in the absorbent article, each of the plurality of sensing elements being formed at least partially of conductive fabric, polymer, and/or printed conductive ink; and at least one adhesive element adapted to adhere the apparatus to (1) the second, outwardly-facing exterior surface of the absorbent article, or (2) to a garment adapted to be worn by the wearer of the absorbent article so that at least part of the apparatus resides between the garment and the second, outwardly-facing exterior surface of the absorbent article; wherein, when the apparatus is adhered to the second, outwardly-facing exterior surface of the absorbent article or to the garment, each of the plurality of sensing elements resides proximate a different, corresponding region of the absorbent article, and is configured to separately detect presence of liquid at the corresponding region.

In some embodiments, at least one of the plurality of sensing elements is configured to detect presence of liquid in the absorbent article based at least in part on a change in capacitance of the absorbent article. In some embodiments, the different regions may be located on a front, a bottom and/or a back of the absorbent article when the absorbent article is worn by the wearer. In some embodiments, the apparatus may be configured for adherence to the second, outwardly-facing exterior surface of the absorbent article, or to the garment. In some embodiments, the apparatus may comprise a signal processing unit which is electrically and mechanically connected to the plurality of sensing elements.

DETAILED DESCRIPTION

The Assignee has appreciated that while various devices exist for separately monitoring a diaper's wetness, or breathing rate, or body temperature, more than one device is conventionally needed to monitor all of the activities of a baby which most parents consider important. The Assignee has also appreciated that attaching multiple sensors to a baby is not only uncomfortable for the baby, but inconvenient for the parent. Further, the Assignee has appreciated that co-locating multiple different sensors may cause some sensors to take inaccurate readings. For example, a breathing sensor is typically placed near where respiration causes lung or body movement, and a diaper wetness sensor is typically placed at a region on an absorbent article that is prone to wetness absorbent articles. Placing a breathing sensor near where a diaper wetness sensor should be located may not yield accurate readings on respiration. Perhaps as a result of these issues, there is presently no single device for providing all desired smart baby monitoring functions.

Absorbent articles such as diapers, training pants, incontinence products, feminine hygiene product, medical garments, surgical pads, and the like conventionally include a liquid permeable body-side liner, a liquid impermeable out cover, and an absorbent core. The absorbent core is typically located in between the out cover and the liner for taking in and retaining liquids (e.g. urine) exuded by the wearer. For an infant or a baby, he or she wears diaper-type absorbent articles daily until turns into three or four years old when he or she goes potty by himself or herself.

Monitoring wetness of absorbent articles is performed so as to change absorbent articles on a timely basis and reduce skin rash. It is important for babies or incontinent persons who may suffer skin rash and some infections like urinary tract infections when they stay with soiled absorbent articles for long periods of time, more importantly for persons who may be unable to communicate with attendants. The present routine in most daycare centers or nursing homes is to check all wearers based on timed interval (e.g. every two hours) for urinary leakage and to change a dry absorbent article when a wetness event is discovered. Although this method of treatment of urinary incontinence helps to maintain absorbent articles of wearers dry, wearers may be unnecessarily disturbed when they are mostly dry and, conversely, may become wet again shortly after being changed. In the first scenario, the absorbent article usage in daycare center is much higher than that at home. At home, parents check diaper more frequently and only change diaper when it is necessary. Care providers change an absorbent article (e.g. diaper) based on timed intervals not wetness levels of an absorbent article. For example, care providers may change a dry or mostly dry absorbent article with very little urine liquid (e.g. peeing once) even the absorbent article is designed to absorb much more urine liquid (peeing more than once, absorbing approximate 40 ounces of water). The higher diaper usage becomes burden for a lot of families who send their children to daycare centers. In the second scenario, an absorbent article may be fully wet before the timed interval (e.g. two hours). A wearer has to keep wearing the fully wet absorbent article until the timed interval is up. It is economically and ecologically necessary to balance the usage or expense of absorbent articles and comfortableness of wearers.

Most of commercial absorbent articles are designed for absorb a certain amount of body liquid (e.g. peeing multiple times) before changing with new and dry absorbent articles. Changing lightly wet absorbent articles or too early may cause increasing usage of absorbent articles and expense of purchasing such absorbent articles. Changing heavily wet absorbent articles or too late may cause skin rush and some infections like urinary tract infections. To detect the wetness level of absorbent articles may balance the cost of purchasing absorbent articles and comfortableness of wearers. Some of external wetness detectors are rigid and bulky. The rigid and bulky detectors may make wearers uncomfortable when the detectors are disposed on wetness prone region of absorbent articles.

Children's potty training is another high demand for parents and/or daycare providers. If an absorbent article is changed based on timed intervals, it is impossible to know exactly when absorbent articles get wet in a daily routine, which is critical for potty training to remind children before wetness event happened.

In the past, many systems of detecting incontinence and other baby conditions have been proposed as a means for informing a parent or attendant that a wetness event has occurred so that the wet absorbent article may be changed to avoid the urine/skin contact and reduce the chances of skin rash.

Monitoring baby's breathing rate is very important to prevent SIDS. The sensor detects baby's breathing rate from his/her belly movement pattern. When the detected breathing rate is lower than 5 times/minute for longer than 15 second. The monitor may alert an attendant or a care provider remotely and immediately.

Additionally or alternatively, a parent may like to learn a baby's growing by monitoring a baby's daily activities, such as diaper status change, sleeping, feeding, rolling over, crawling and walking.

The Assignee has thus appreciated that a smart baby monitoring system with wetness detection which may monitor a baby's breathing rate, sleeping pattern, body position, rolling over, crawling, walking activities, evaluate the wetness level of an absorbent article and record historical events (e.g. wetness, breathing, feeding, etc.) is desirable. Accordingly, some embodiments of the present invention are directed to a smart baby monitor system with wetness detection to monitor a baby's breathing rate, body temperature, daily activities and the status of an absorbent article, alert a parent, care provider or attendant to a low breathing rate (e.g. less than 5 times/minute) and/or wet absorbent article condition and provide a wet event time pattern by which young children may be potty trained. The smart baby monitor system may comprise a) a housing including at least a sensor, and an electrical powered signal processing unit can wirelessly transmit signal to an attendant and b) a flexible wetness sensing element outside of the housing. The wetness sensing element may be flexible, stretchable and washable and made of polymer, metal sheet, woven or nonwoven fabric and/or textile. The polymer can be plastic, rubber, and/or materials made of polymer, or other polymer materials now known or later invented.

The wetness sensing part may be outside of monitor housing and needs to be comfortable, flexible, stretchable and/or made of fabric-type (e.g. textile) and/or flexible polymer type of materials (e.g. silicone, rubber). The breathing rate, low breathing rate alert, sleeping pattern, body temperature, a baby's activities and wetness event signals may be sent to an attendant or care provider wirelessly including but not limited to Bluetooth, WiFi, Zigbee and Z-wave and radio frequency (RF).

In some embodiments, the flexible wetness sensing element may comprise a conductive strip stacked on a non-conductive strip. The conductive and non-conductive strips may be made of fabric, metal or polymer. The flexible sensing element may be attached or adhered to an absorbent article to sense capacitance variation. When an absorbent article turns to wet, the dielectric constant of the wet absorbent article changes so that the capacitance between the sensing element and the absorbent article changes. Once the capacitance value is above a threshold value, the wetness detector records a wet event and sends a notification to attendant's phone or computer immediately so that the diaper may be changed.

The flexible sensing element may be attached to an absorbent article with an adhesive manner including but not limited to button, clamp, clip, zip and/or hook-like type. The sensing element may be attached/adhered to a garment or cloth facing and adjacent to an absorbent article. A garment may, for example, be pant-like, such as jeans, shorts or underwear, a "onesie," etc., but does not include an absorbent article.

In some embodiments, the flexible wetness sensing element may comprise a sandwich stacked structure with non-conductive strip in the middle and two conductive strips on top and bottom, respectively. The non-conductive strip may be made of fabric, polymer or any known or later invented flexible material. The two conductive strips may be made of metal sheets, conductive polymer, and conductive fabric or made by sewing/stitching conductive filament into non-conductive strips to form patterns including but not limited to mesh, grid, rectangle, square, ellipse, pie shape, circle. The stacked sandwich structure may be pressed or overmolded together, such as with adhesive glue and/or injection and/or thermal process and/or being sewed or stitched with non-conductive filament. The flexible sensing element may be attached to an absorbent article with an adhesive manner including but not limited to button, clamp, clip, zip and/or hook-like type. The sensing element may be attached to a garment or cloth facing and adjacent to an absorbent article. One conductive strip may be wider and/or longer than the other conductive strip along all directions. The conductive strip with larger area, also named as shield strip, shields noise or unwanted signal other than wetness detection. The conductive strip with smaller area, also named as sensing strip, may sense capacitance change when an absorbent article is wet. In some embodiments, the sensing strip may be attached to a Velcro hook strip, which is attached to an absorbent article for use. In some embodiments, the shield strip is attached to a Velcro hook strip, which is attached to garment or cloth facing and adjacent to an absorbent article. The sensing strip may or may not touch an absorbent article.

The electrical powered wireless sensor-transmitter comprises an analog to digital convert, a microcontroller and a wireless transmitter, including but not limited to RF, Bluetooth, WiFi, Z-wave and/or Zigbee protocol. The wetness sensing element may be mechanically and electrically connected to wireless sensor-transmitter preferably by soldering, sewing, winding, physical molding, pressing, clamping, and/or touching. The wetness sensing element may be electrically attached and detached from signal processing unit by using buttons, clips, clamps, when the wetness sensing element needs to be replaced.

Some embodiments of the invention may employ multiple smaller sensing elements, rather than one larger sensing element. These smaller sensing elements may be laid out on one side of nonconductive strip with space between/among adjacent conductive strips. These smaller sensing elements may be electrically isolated. Each individual sensing element may be considered as one sensing element, and each may monitor a different region which is prone to wetness. When diaper is partially wet, part of wetness prone region is wet, remaining part of wetness prone region is dry. For sensing elements located at wet region, their capacitance values are above wetness capacitance threshold value. For sensing elements located at dry region, their capacitance values remain no change or are lower than wetness capacitance threshold value. For sensing elements located across wet and dry regions, their capacitance values may increase above or below wetness capacitance threshold value. By monitoring individual location of wetness, wetness level of a whole diaper may be evaluated and wirelessly transmitted to alert attendant. Attendant may decide to change the wet diaper immediately if the diaper is fully wet or wait for a while if the diaper is just partially wet to avoid unnecessary diaper change and reduce the usage of diaper.

In some embodiments, a wetness sensing element may comprise pairs of conductive filaments sewed into nonconductive stretchable fabric. One filament of a pair may be sewn in a zigzag pattern. The other filament of the same pair is sewed zigzag but with opposite direction so that one filament is electrically and physically separable from each other. Two conductive filaments only have points overlap but on top and bottom sides of nonconductive strip, respectively. When the stretchable fabric is attached to a dry absorbent article, capacitance between two conductive filament is minimal. When the absorbent article is wet, the surface of absorbent article expands as well as the attached wetness sensing element so that the two zigzag stitching filaments stretch and result in capacitance change. The capacitance between two conductive filaments changes is due to overlap area between two filaments change. The capacitance change is monitored by electrical powered wireless sensor-transmitter and transmitted to alert attendant.

In some embodiments, a wetness sensing element may comprise conductive and non-conductive polymer layers with different patterns in a form of mesh, grid, multiple parallel lines and/or solid shapes.

In some embodiments, multiple off-shelf wetness sensors that may be used to detect wetness, e.g. humidity sensor, optical sensors, ultrasonic sensors, may be soldered or sewed in non-conductive woven fabric with a conductive filament.

In some embodiments, multiple off-shelf inertial sensors, optical sensors and/or chemical sensors may be integrated into a smart monitoring system to monitor not only wetness but also a fecal insult, breathing rate, sleep pattern, body positions, rolling, walking and/or crawling activities.

In some embodiments, a wireless transmitter may only be powered on when needed to send a signal out. In other words, most of time the wireless transmitter may be off unless an event causes it to wake, such as sensing low breathing rate (less than 5 times/minute) or a wet absorbent article. A transmitter which is powered on when triggered by an event may reduce power consumption and produce low radiation.

Some embodiments of the invention may record wetness events of absorbent articles and other events, such as low breathing rate, feeding and sleeping, daily with specific hours and minutes in smart phone or computer. The pattern of daily wetness may be used for children's potty training or statistics of absorbent articles usage. For example, one child may routinely go potty a first time in the morning around 9 am, a second time around noon, a third time around 3 pm, a fourth time around 6 pm and a fifth time around 9 pm. For potty training purpose, a parent or care provider may remind young children to go potty before their routine wet time. The wetness record may statistically indicate how many diapers are used daily, weekly, monthly or yearly.

It should thus be appreciated that some embodiments may provide an improved smart baby monitor system for not only monitoring a baby's breathing rate, body temperature, activities but also detecting and signaling a wet diaper condition quickly, reliably, economically, ecologically, and conveniently. In some embodiments, a wetness detector may detect not only whether an absorbent article is wet but also the wetness level of the absorbent article (lightly wet, or heavily wet). (In this respect, the term "wetness" is used herein to denote the presence of liquid within an absorbent article, whether or not the surface of the absorbent article is wet to the touch.) The wetness detector may also, or alternatively, indicate a wet region on an absorbent article, e.g. front, bottom or back. The components of the wetness monitoring system may be designed so as to be easily removed and reused. For example, in some embodiments, a sensing element may be washed, mopped or replaced when it gets soiled.

Some embodiments may provide great advantages in the care of young children or incontinent people since they may allow a wet absorbent article to be changed timely and economically, thus reducing instances of urine induced skin rash while also avoiding excessive usage of absorbent articles. The detector system may be further advantageous in potty training since it may record historical wet events with a routine time related pattern. The detector system may predict future potty events and remind young children to go potty before wetting pants or clothes. In this manner, the child makes the mental connection between wetting and the toilet much quicker than with older fashioned toilet training techniques.

Some embodiments may provide detailed information about a baby's breathing rate, sleep position, sleep/nap time pattern, rolling, crawling and walking activities and give parents a peaceful mind and information of a baby growth.

In some embodiments, a smart diaper monitoring system may be attached, adhered or otherwise disposed on an outwardly-facing exterior surface of a diaper-type absorbent article. To monitor a baby's breathing, the breathing sensor may be disposed on the exterior surface absorbent article around the baby's belly area. To monitor diaper wetness level, the wetness sensor may be disposed on wetness prone region of diaper. The wetness sensor and other sensors (e.g. inertial sensor and temperature sensor) are connected together with a manner of flexible, stretchable and/or conductive material (e.g. conductive fabric and/or polymer) to make a wearer comfortable.

Some embodiments may comprise a detector that can detect a wetness event (e.g. the presence of urine) in an absorbent article. The wetness detector may evaluate the wetness level of an absorbent article and notify a care provider, an attendant or a user whether an absorbent article needs to be changed immediately or later. The absorbent article is designed to absorb certain amount of liquid. By evaluating the wetness level in an absorbent article, a user may achieve a balance between the usage of absorbent articles and a wearer's minimal uncomfortableness (e.g. skin rash). In this manner, some embodiments provide advantages over wetness detecting systems which are incorporated within absorbent articles, as known in the art. In some embodiments, a detector may indicate a wetness location (i.e. front, back and/or bottom) in an absorbent article.

The smart baby monitoring system may be removably or reversibly attached to and detached from a wearable item (where a wearable item comprises any object that a person may wear), so that at least part of the smart baby monitoring system resides between a wearable item and an exterior surface of an absorbent article. In some aspects a wearable item may be worn by animals other than people, including but not limited to dogs, cats, services animals, or other animals. A wearable item may be an absorbent article, including but not limited to a diaper, a toddler diaper, a pull-up, or an adult diaper. The wetness sensing apparatus may be reversibly attached to the wearable item, being an absorbent article, at an outer surface or an inner surface of the absorbent article. A wearable item may be an article of clothing or other object worn by a user, including but not limited to underwear, pants, shorts, pantyhose, a skirt, a dress, a kilt, or other item, any of which are referred to herein as a garment. The wetness sensing apparatus may be disposed on a garment facing and adjacent to an absorbent article by a manner including but not limited to hook type fastener, adhesives, buttons, clamps, snaps or other mating fasteners. In other aspects, the wetness sensing apparatus may be disposed on a wearable item without the use of an absorbent article. When the wetness sensing apparatus may be disposed on a wearable item facing and adjacent to an absorbent article, the wetness sensing apparatus may touch the absorbent article but does not require detachment from or re-attach to the wearable item when a user needs to change the absorbent article.

Throughout the present disclosure, the wetness sensing apparatus may be referred to as a smart baby monitor system, a smart baby detector, and/or a wetness detector system.

Figure 1A:
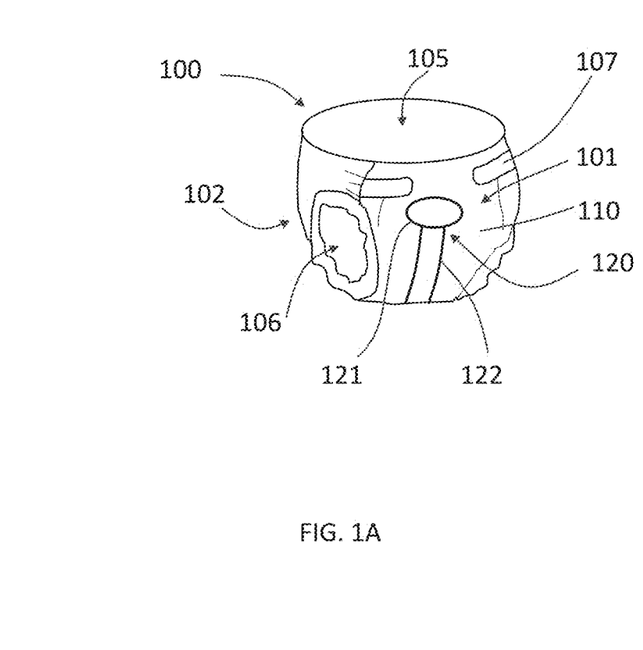
FIG. 1A depicts a front-fastenable diaper type absorbent article with detector attached in front of absorbent article, in accordance with some embodiments of the invention.
Figure 1B:
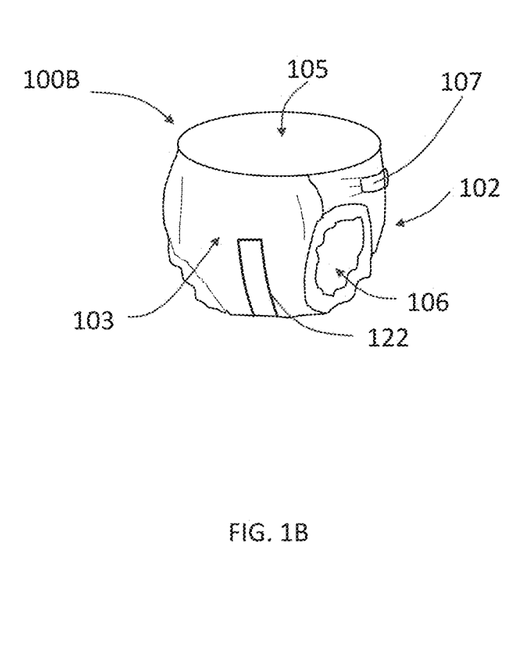
FIG. 1B depicts a front-fastenable diaper type absorbent article with sensing strip extended to the back of an absorbent article, in accordance with some embodiments of the invention.

A representative absorbent article 100 is shown in FIG. 1A and FIG. 1B. While the description herein makes various references to a diaper, it should be appreciated that embodiments of the invention are not limited to being used only with a diaper, and that embodiments may be employed with any of numerous types of absorbent articles, including but not limited to diapers, training pants, incontinence products, feminine hygiene product, medical garments, surgical pads, and the like without departing from the scope of the present disclosure. It should also be understood that embodiments are not limited to detecting the presence of liquid, and may be used to identify the presence of an insult in a garment with or without an absorbent article being present.

FIG. 1A illustrates an outside perspective view of a front 101 and a side 102 of a diaper-type absorbent article 100 adapted for wearing by a subject. FIGS. 1A-1B depict that the diaper-type absorbent article 100 may include a waist opening 105, leg openings 106, one or more front fasteners 107, a front garment-facing layer 110. When worn by the subject (i.e., so that the legs of the subject reside within leg openings 106 and the front fastener(s) 107 cause(s) waist opening 105 to encircle the subject's waist), absorbent article 100 includes one exterior surface which comes into contact with, and is closer to the subject than, the subject, and another, opposing exterior surface which is farther away from the subject. For example, in the example shown in FIG. 1A, the exterior surface which is farther away from the subject when the absorbent article 100 is worn may coincide with the garment-facing layer 110.

A wetness detector system 120 may be longitudinally disposed on front garment-facing layer 110 and be removed from the absorbent article 100 by manners include but not limited to hook-like, button, clamp, clip and/or zip type. A gap between the wetness detector system 120 and the absorbent article 100 may be no more than 10 mm, and or no more than 5 mm. For commercial brand diaper-type absorbent articles, the wetness detector 120 may be aligned with a printed pattern in the diaper-type absorbent articles. For cloth type absorbent articles, the wetness detector 120 may be disposed longitudinally in the center of front 101. The wetness detector system 120 comprises a signal processing unit 121 and a wetness sensing element 122. The signal processing unit 121 may be disposed at the location where the inertial sensor inside of 121 can sense the body movement due to respiration. The wetness sensing element 122 may be disposed at a wet prone region on an absorbent article 100 or a garment facing an absorbent article. The wetness sensing element 122 may be a capacitive, resistive, inductive, optical sensing. In a preferred embodiment, the wetness sensing element 122 is capacitive sensing. The sensor's capacitance value may change when absorbent article 100 is wet. The wetness sensing element 122 is electrically connected to the signal processing unit 121. The signal processing unit 121 reads the capacitance value of the wetness sensing element 122 and converts the capacitance value to frequency, current or voltage value and wirelessly transmits to a phone or computer. When the capacitance value is higher than a wetness threshold value, the phone or computer may show an alert of message, voice or vibration. The wetness event may be recorded in cloud. As depicted in FIGS. 1A and 1B, wetness detector 120 may have physical dimensions enabling one end of wetness sensing element 122 to be adhered to the front 101 and the other end of wetness sensing element 122 to be adhered to the back 103.

FIG. 1B illustrates an outside perspective view of a side 102 and a back 103 of a diaper-type absorbent article 100B formed for wearing. The diaper-type absorbent article 100B may include a waist opening 105 and a leg opening 106. Detector 120 system may be longitudinally extended in the back 103. In another variation of embodiment, the wetness detector system 120 may be attached to the back 103 and/or the wetness sensing element 122 may be extended to front 101.

Throughout the present disclosure, a reference to a diaper-type absorbent article can refer to a pant-type absorbent article or a cloth type absorbent article.

Figure 2A:
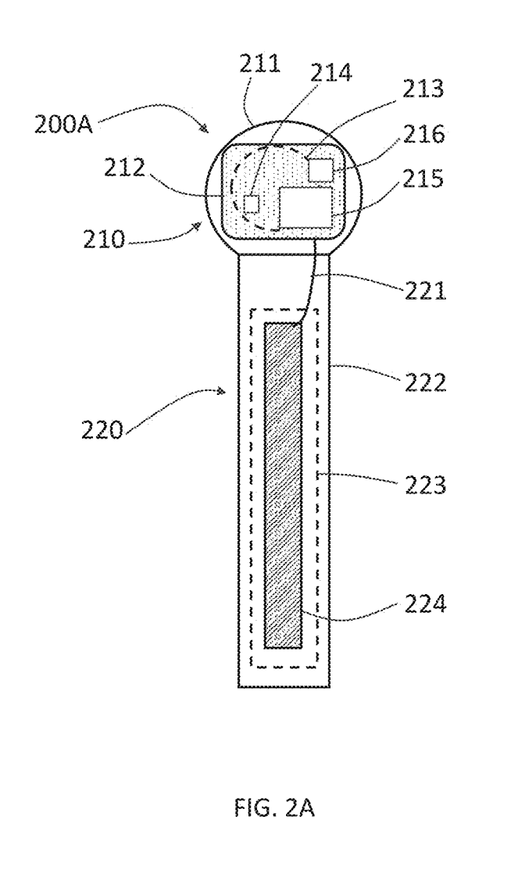
FIG. 2A depicts a top plan view of a wetness detector including a single sensing strip in its assembled condition, in accordance with some embodiments of the invention.

FIG. 2A illustrates a wetness sensing apparatus 200A that comprises a signal processing unit 210 and wetness sensing component 220. As best illustrated in FIG. 2A, the wetness sensing component 220 is electrically and mechanically connected to the signal processing unit 210. The wetness sensing component 220 may be molded, stitched, snapped, clamped, pressed or soldered to the signal processing unit 210. The wetness sensing component 220 may also be electrically stitched, sewed or wound with conductive filament to the signal processing unit 210. The wetness sensing component 220 may be removed and/or replaced from the signal processing unit 210. The signal processing unit 210 comprises a housing 211, an electrical board 212 with at least an electrical component 214, an integrated circuit 215, and an electrical power source 213, an analog to digital converter 214, a microcontroller 215 and a wireless transmitter 216. The housing 211 may be made of a polymer material with Shore A number less than 100. The housing 211 may be sealed and/or waterproof. The housing 211 may be covered with soft materials include but not limited to fabric or polymer. The electrical component 214 can be passive or active electrical component or sensors, e.g. inertial sensor, temperature sensor, optical sensor, chemical sensor. The electrical power source 213 may be a rechargeable or non-rechargeable battery including but not limited to a lithium coin battery or a lithium chargeable battery. The electrical power source 213 may be an energy harvester converting thermal, mechanical, solar, chemical, biological or physical energy to electrical power. For example, an energy harvester may convert human motion energy to electrical power to supply the wetness detector system. In this manner, the power source 213 does not require being changed or charged externally. In some aspects, the power source 213 may be in a second separate housing and electrically connected to the housing 211 through flexible connector. In a preferred embodiment, the sensing component 220 is capacitive sensing. The capacitance value changes due to an absorbent article's dielectric constant changing while absorbing water. The sensing component 220 comprises at least one sensing conductor 224 and/or a non-conductive strip 222. The non-conductive element 222 may be flexible, washable, or stretchable, and the non-conductive strip 222 may be made of fabric and/or polymer. The non-conductive element 222 may have a proximal side, being a side of the non-conductive element 222 to be placed closer to the user, and a distal side, being a side of the non-conductive element 222 to be placed away from the user. The thickness of non-conductive strip 222 is at least 0.2 mm. The conductive element 224 may be conductive fabric, polymer, metal sheet or printed conductive ink with rectangular, square, circular, pie-shape, elliptic, mesh, grid, wire or irregular shapes sensing impedance change when an absorbent article is wet, and may be flexible. The sensing strip 224 may be made of sewing or winding a conductive filament into non-conductive strip in the form of mesh, grid, and rectangular, circular shapes. A conductive filament may comprise a plurality of thread comprising fabric or metal or other conductive material, or may comprise a plurality of polymer lines or strands, or may comprise a plurality of 3-D printed materials, also referred to as additive manufacturing, or may comprise flexible conductive materials now known or later invented. The sensing strip 224 may be made of pressing conductive polymer into nonconductive polymer in the form of mesh, grid, and rectangular, circular, oval shapes.

In some embodiments, the wetness detector system may include but not limited to an inertial sensor, a temperature sensor, a gas sensor, a chemical sensor, an optical sensor or an off the shelf wetness sensor.

In some embodiments, the sensing component 220 may comprise at least one sensing strip 224, a non-conductive strip 222 and a shield strip 223. The shield strip 223 may be at least 0.2 mm wider in all direction than the sensing strip 224. There may be a 0.2 mm to 5 mm gap between the shield strip 223 and the sensing strip 224. The non-conductive strip 222 may be flexible, washable or stretchable and made of fabric and/or polymer. The sensing strip 224 may be separable from shield 223 by non-conductive strip 222. The thickness of non-conductive strip 222 may be at least 0.2 mm. The sensing strips 224 and shield strip 223 may be conductive fabric, polymer, metal sheet or printed conductive ink with rectangular, square, circular, pie-shape, elliptic, mesh, grid, wire or irregular shapes sensing impedance change when an absorbent article is wet. The sensing strip 224 and shield strip 223 may be made by sewing or winding conductive filament into a non-conductive strip or pressing conductive polymer into non-conductive polymer. When the wetness detector system 200A is attached to an absorbent article, the sensing strip 224 may be facing or closer to absorbent article than shield strip 223, and the shield strip 223 is facing or closer to a garment or cloth. The wetness detector system 220A may be attached to an absorbent article by manners include but not limited to hook-like, button, clamp, zippers, magnets, clip and/or zip type. In another variation of attachment, the wetness detector 200A may be attached to a garment facing or adjacent to an absorbent article. The wetness sensing component 220 is electrically connected to a signal processing unit 210 by conductive filament 221, pins, metal wires or pads. The wetness sensing component 220 is assembled to the signal processing unit 210 including but not limited to molding, pressing, soldering, sewing, winding, knotting, clipping, snapping and clamping.

Figure 2B:
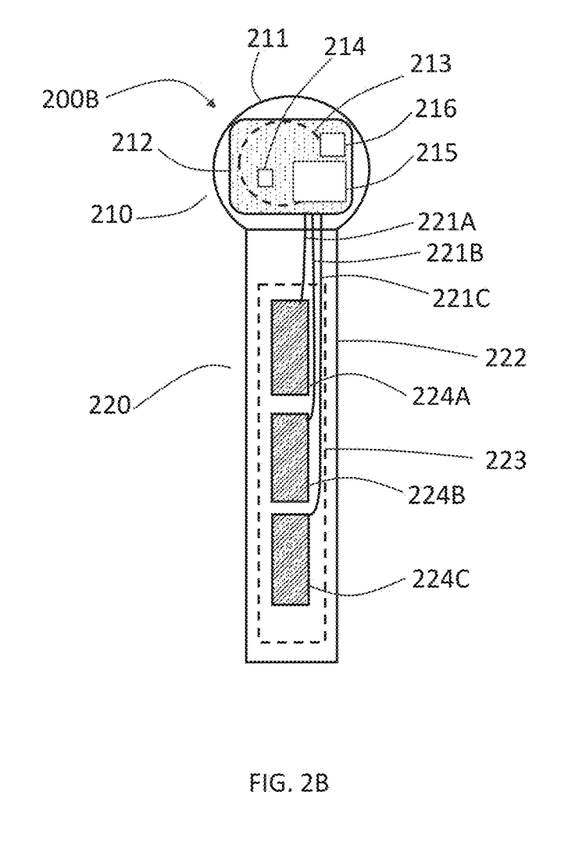
FIG. 2B depicts a top plan view of a wetness detector with plural sensing elements in its assembled condition, in accordance with some embodiments of the invention.

FIG. 2B depicts a wetness detector 200B comprising a signal processing unit 210 and wetness sensing component 220. A wetness sensing component 220 comprises a plurality of sensing elements 224A, 224B and 224C. Although three sensing elements are shown in FIG. 2B, any suitable number of sensing elements may be provided. The sensing elements 224A, 224B and 224C may be made of materials such as metal foil, conductive polymer, conductive fabric or non-conductive fabric sewed with conductive filament. The shape of conductive strips 224A, 224B and 224C may be rectangle, square, triangle, pie, circle, mesh or grid. The sensing elements 224A, 224B and 224C may be electrically isolated from each other and connected individually to different channels in the signal processing unit 210 through connector 221A, 221B and 221C, respectively.

The conductive strips 224A, 224B and 224C may be at different locations on a non-conductive strip 222 and separately sense wetness of an absorbent article at different regions. For example, if sensing elements 224A, 224B and 224C cover an absorbent article front, bottom and back, respectively, sensing element 224A may detect wetness in the front of the absorbent article, sensing element 224B may detect wetness at the bottom, and sensing element 224C may detect wetness in the back. In this respect, a "wet" absorbent article may only be using a portion of its absorbent capacity, and may not require changing immediately. As a result, in some embodiments, a user may not be informed if only sensing element 224A (or another of sensing elements 224B-224C) detects wetness in the front of the absorbent article, but rather, the user may only be informed if more than one of sensing strips 224A-224C detect wetness in their respective regions. Because a user may not be prompted to change the absorbent article immediately, the user can appropriately balance the usage (and thus cost) of absorbent articles and the comfortableness, hygiene and health of the wearer.

Figure 3A:
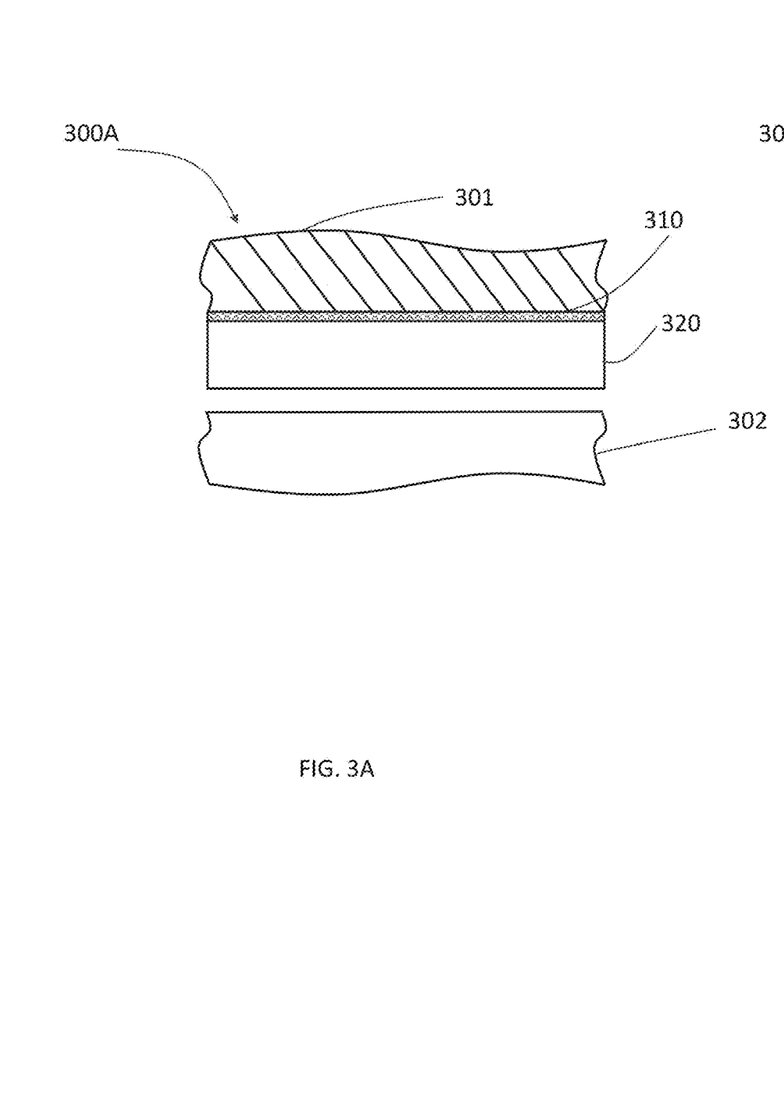
FIG. 3A is a cross-sectional view of the wetness detector attached to an absorbent article, in accordance with some embodiments of the invention.
Figure 3B:
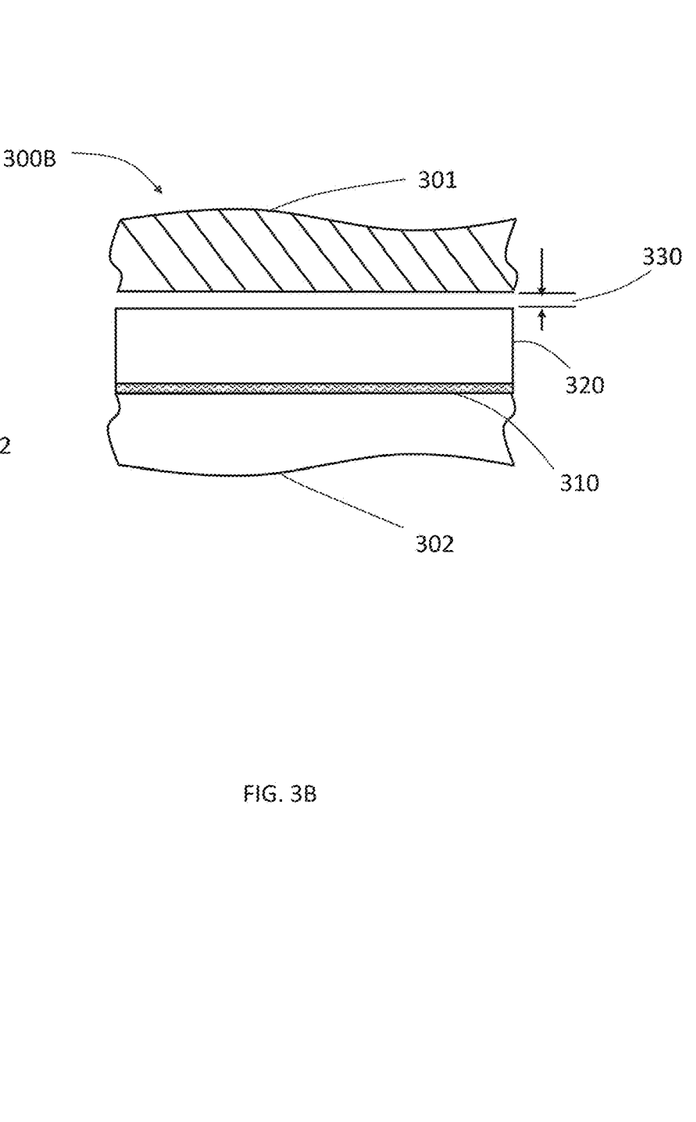
FIG. 3B is a cross-sectional view of the wetness detector attached to a garment facing and adjacent to an absorbent article, in accordance with some embodiments of the invention.

FIGS. 3A and 3B depict various ways of attaching or assembling a wetness detector system. FIG. 3A depicts a wetness detector system 320 being attached or disposed between an absorbent article 310 and a garment 302 is attached to an absorbent article 310 with a hook-like adhesive layer 310. In different variations of present invention, the sensing element 320 may be attached to an absorbent article 301 with other manners including but not limited to clip, clamp, zip, magnet, adhesive bond. The sensing element 320 may be capacitive sensing, inductive sensing, resistive sensing, optical sensing or ultrasonic sensing. In the example shown in FIG. 3A, in which the wetness detector system 320 is adhered to an exterior surface of absorbent article 301, when the absorbent article 301 becomes wet, wetness detector system 320 may be detached from the absorbent article 301, and later attached to another dry absorbent article.

The Assignee has appreciated that when a wet absorbent article is changed, the detector 320 may be accidently thrown away together with a wet absorbent article 301 when a care provider or attendant forgets to detach the detector 320 from the wet absorbent article 301. To address this, FIG. 3B illustrates the wetness detector 320 being attached to a garment 302 facing an absorbent article 301 with an adhesive layer 310 (e.g., by hook-like, clip, clamp, zip, magnet, and/or adhesive bond). The detector 320 lies against and is facing to absorbent article 301. The detector 320 may or may not touch the absorbent article 301. The gap 330 between a wetness detector 320 and an absorbent article 301 is less than 10 mm or less than 5 mm. One advantage of attaching detector 320 on garment 302 is that when a wet absorbent article 301 is changed, detector 320 need not be detached and then re-attached to another absorbent article, since it is attached to a garment 302 and not the absorbent article 301. This reduces the burden imposed on an attendant or a care provider to detach and re-attach the wetness detector 320 every time an absorbent article is changed. It also prevents an attendant from accidently disposing of a wetness detector 320 with the wet absorbent article.

A wetness sensing element may be in the housing of signal processing unit. The wetness sensing element may be outside of the signal processing housing. A wetness sensing element may be capacitive, resistive, inductive, optical, chemical and physical sensing manner.

Figure 4A:
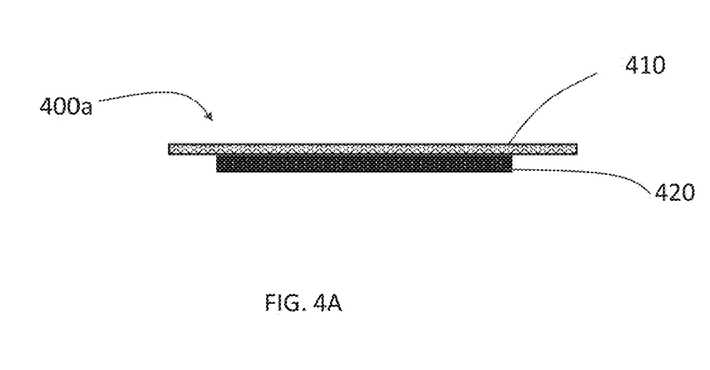
FIG. 4A-E are cross-sectional views of various sensor configurations, in accordance with some embodiments of the invention.

FIG. 4A-E depict cross-sectional views of various wetness sensing element designs. FIG. 4A illustrates a capacitive wetness sensing element 400a comprising an adhesive layer 410 and a conductive layer 420. In some embodiments, layers 410 and/or 420 may be flexible, stretchable and washable.

Figure 4B:
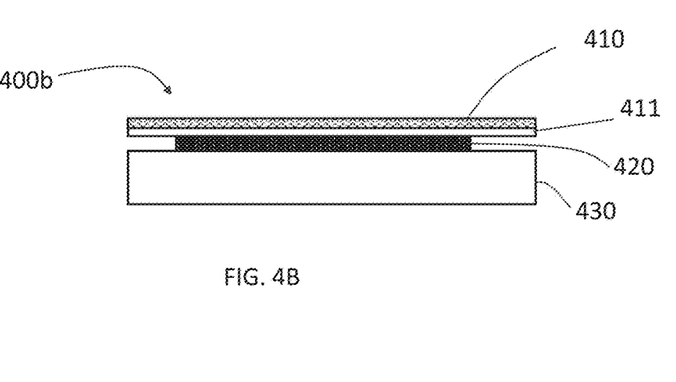

FIG. 4B illustrates a capacitive wetness sensing element 400b comprising an adhesive layer 410, a conductive layer 420 between the nonconductive layer 411 and a nonconductive layer 430. Layers 410, 411, 420 and 430 may be flexible, stretchable and washable. A non-conductive layer 411 may or may not be required. Layer 410 and 420 may, for example, be less than 2 mm thick. Layer 430 may, for example, be more than 0.2 mm thick or more than 2 mm thick. The adhesive layer 410 may be attachable and removable from an outer surface of an absorbent article.

Figure 4C:
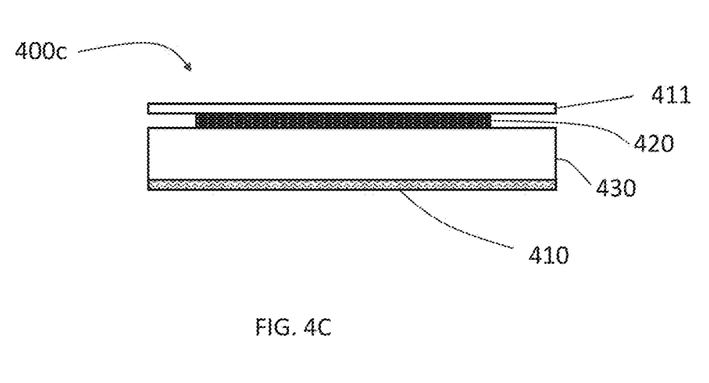

FIG. 4C shows an adhesive layer 410 is attached on the opposite side of nonconductive layer 430 as in FIG. 4B. In FIG. 4C, the wetness sensing element 400c may be configured for attachment to a garment, facing or adjacent to an absorbent article. A non-conductive layer 411 may or may not be required.

Figure 4D:
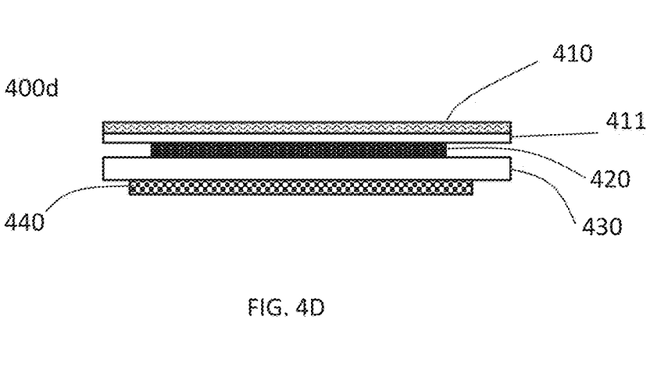

FIG. 4D depicts a wetness sensing element 400d comprising an adhesive layer 410, a nonconductive layer 411, a conductive layer 420, a non-conductive layer 430, and a conductive shield layer 440. Conductive layers 420 and 440 may each be made of fabric, polymer or metal. The adhesive layer 410 may be configured to face an absorbent article. The conductive shield layer 440 may shield unwanted signal from wetness signal and is facing garment. A non-conductive layer 411 may or may not be required. The adhesive layer 410 may be facing a garment as shown in FIG. 4C.

Figure 4E:
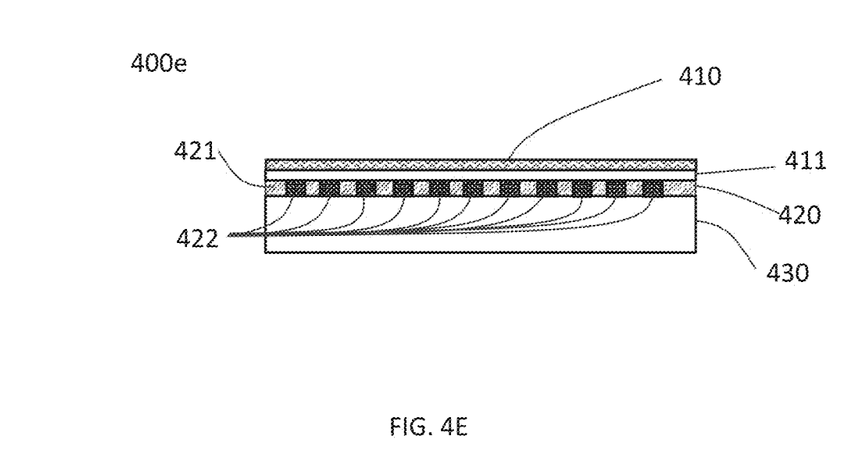

FIG. 4E depicts a wetness sensing element 400e comprising an adhesive layer 410, a non-conductive layer 411, a sensing layer 420, and a non-conductive layer 430. A sensing layer 420 comprises a conductive filament 422 and non-conductive layer 421. A conductive pattern 422 is molded, pressed and/or embedded into a non-conductive layer 421. A conductive filament 422 may be sewn into nonconductive layer 421 to form a patterned sensing layer 420. The conductive filament 422 may be mesh, grid, rectangle, square, circle, pie or ellipse shape.

Figure 5A:
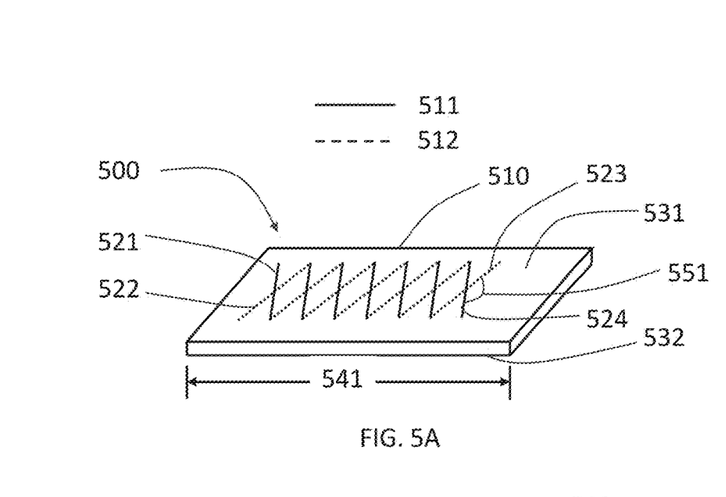
FIG. 5A and FIG. 5B depict a stretchable wetness sensor sensing stretch movement, in accordance with some embodiments of the invention.
Figure 5B:
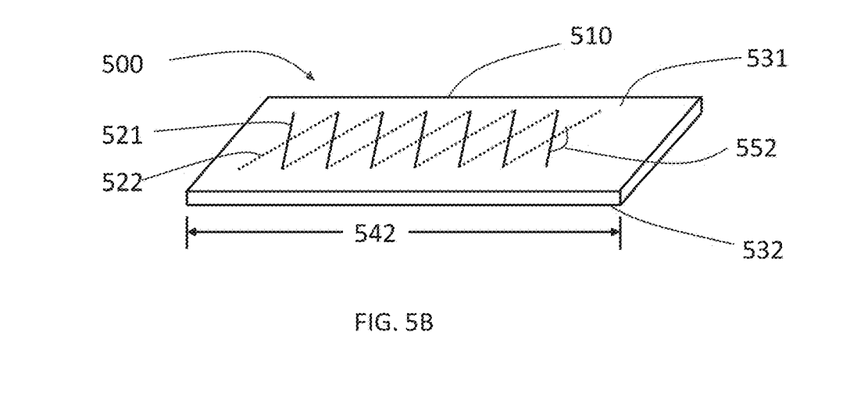
Figure 5C:
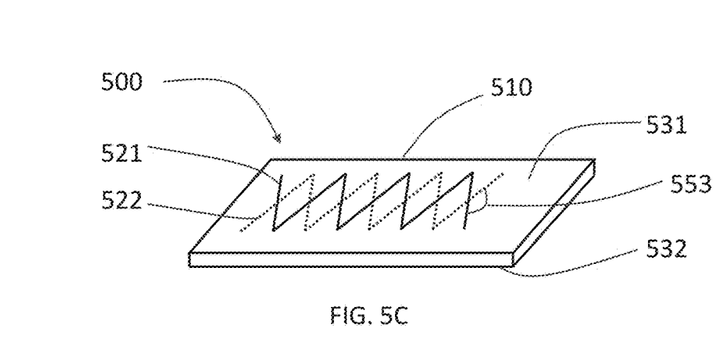
FIG. 5C depicts another stretchable wetness sensor configuration, in accordance with some embodiments of the invention.

In some embodiments of the invention, a wetness sensor may be configured to stretch if and when an absorbent article to which it is attached or juxtaposed enlarges or swells as a result of absorbing liquid. For example, in some embodiments, a sensor may be configured to detect swelling or enlargement of an absorbent article, and stretch to accommodate it. FIGS. 5A-C depict various stretch sensor designs.

FIG. 5A depicts an original shape of a stretchable sensor 500 before stretch. Conductive filaments 521 and 522 are embedded into a non-conductive stretchable layer 510. The conductive filaments 521 and 522 is made of fabric, polymer or metal wire. The conductive filament 521 is electrically isolated from the conductive filament 522. The solid lines 511 and dashed lines 512 are located on top and bottom surface of stretchable strip 510, respectively. The non-conductive strip 510 has a first surface (top surface) 531 and a second surface (bottom surface) 532. The conductive filament 521 is stitched into the first surface 531 of non-conductive fabric 510, may run a more than 1 mm long filament segment on the first surface 531, is then stitched into a second surface 532, may run a more than 1 mm long filament segment on second surface 532 with a smaller than 90 degree angle from the previous filament segment, and is then stitched back to the first surface 531 with the same angle as the previous filament segment, and so on. The conductive filament 522 is firstly stitched into a second surface 532 of non-conductive strip 510, may run a more than 1 mm long filament segment on a second surface 532, is then stitched into first surface 531, may run a more than 1 mm long filament segment on a first surface 531 with a smaller than 90 degree angle from the previous filament segment, is then stitched back to the second surface 532, and so on. In some embodiments, there may be no physical or electrical contact between filament 521 and filament 522. Rather, the filament 521 and filament 522 are interleaved on opposing surface 531 and 532 of non-conductive strip 510. An angle 551 between filament segment 523 and filament segment 524 may be, for example, from 120 to 180 degrees.

In some embodiments, a stretchable sensor may be wrapped with a conductive shield on an outer surface, such as to block unwanted signals.

When a stretchable sensor 500 is stretched, the length 541 of stretch sensor 500 in FIG. 5A may change to length 542, as shown in FIG. 5B. When this occurs, the angle 551 between filament segments 523 and 524 in FIG. 5A may change to 552, as shown in FIG. 5B. When stretching occurs, the capacitance between two conductive filaments 521 and 522 may change, due to varying fringing electrical field and overlap area. The capacitance change in this manner may be not due to dielectric constant change, as described previously.

A stretchable sensor may stretch in response to various stimuli, only some of which relate to swelling or enlargement of an absorbent article due to absorbing liquid. For example, in some embodiments, stretching may result from belly movement, waist size change, stretched elastic band, etc.

FIG. 5C depicts a variation on the examples shown in FIGS. 5A-5B.

Specifically, in this variation, conductive filament 521 is laid on the surface 531 of stretchable strip 510, and a conductive filament 522 is laid on the surface 532 of stretchable strip 510. In some embodiments, stretchable strip 510 may be non-conductive.

Figure 5D:
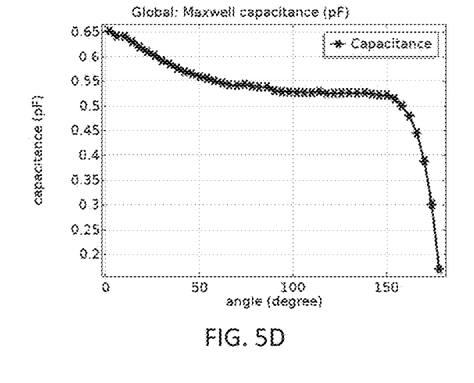
FIG. 5D is a graph depicting a capacitance change when a stretchable wetness sensor is stretched, in accordance with some embodiments of the invention.

FIG. 5D depicts capacitance change versus an angle "theta" (e.g., angles 551 and 552). The angle "theta" is preferably between 150 degree and 180 degree, but may be between 0 degree and 180 degrees.

The stretchable sensor as shown in FIG. 5 may be used to monitor breathing rate by detecting the belly movement. The stretchable sensor is attached to region of diaper or clothing close to belly. When a person is breathing, his/her belly size is changing following with breathing pace. The changed belly size may stretch the sensor.

Figure 6A:
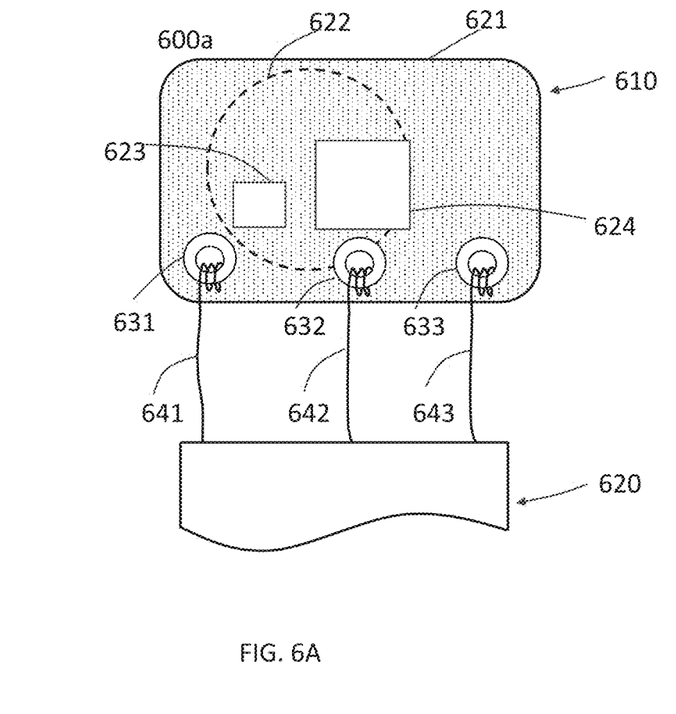
FIGS. 6A-6B are schematic assembly views of a sensor electrically connected to signal processing units, in accordance with some embodiments of the invention.
Figure 6B:
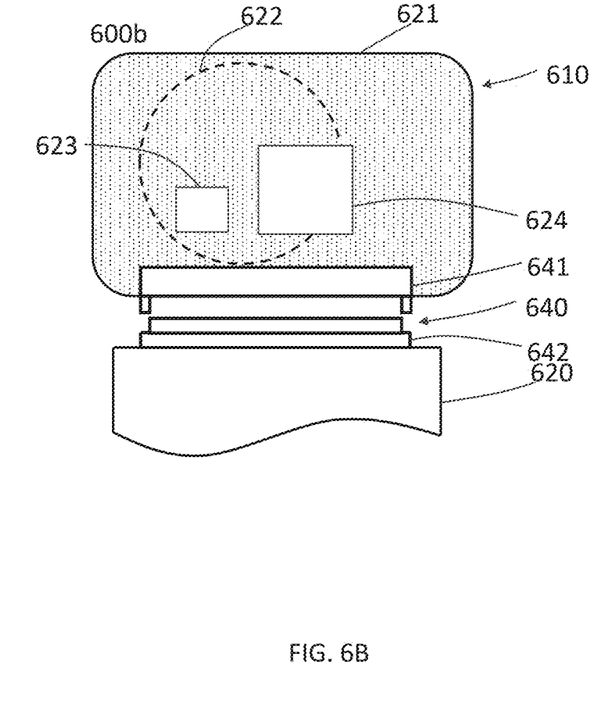

FIGS. 6A and 6B depict various configurations of a signal processing unit 610 and a wetness sensing element 620. As can be seen from FIG. 6A, the signal processing unit 610 comprises a board 621, an electrical power source 622, at least an electrical component 623, at least an integrated circuit 624 and electrical contact ports 631, 632, 633 coated with conductive material. These conductive ports 631, 632 and 633 may pass signals from sensing element 620 to a board 621. The board 621 may be rigid, flexible or rigid-flexible. The conductive filaments 641, 642 and 643 are respectively soldered or wound into the contact ports 631, 632 and 633. The winding manner includes but not limited to knotting, stitching, clamping, wedging, clipping or rolling manner, as long as the objective of electrical connection is achieved. In addition, an extra conductive or nonconductive filament, strip, tape or glue may be added at the windings to ensure the stability and durability of electrical and mechanical connection thereof. Furthermore, the conductive ports 631, 632, 633 are electrically connected to conductive filaments 641, 642 and 643 in one-to-one manner. The conductive wire may include but not limited to conductive filaments, metal wires, weaved conductive and non-conductive filaments with resistivity less than 100 ohm·cm or less than 10 ohm·cm. In another embodiment, the wetness sensing element 610 may be replaced, detached from signal processing unit 620.

FIG. 6B depicts another variation of wetness detector assembly. A connector 640 is formed to electrically connect a sensing element 620 to a signal processing unit 610 by a manner including but not limited to a plug 642 and socket 641 mating type. A plug 642 may be integrated in sensing element 620. A socket 641 may be integrated in signal processing unit 610. A plug 642 may be integrated in signal processing unit 610. A socket 641 may be integrated in sensing element 620. A socket 641 is an opening into which a plug 642 is designed to fit while plug 642 is a pronged connecting device which fits into a mating socket 641. A connector 640 may be configured as pogo pins, which may be soldered in signal processing unit 610. The pogo pins may be pressed and electrically contact a sensing element 620.

Figure 7:
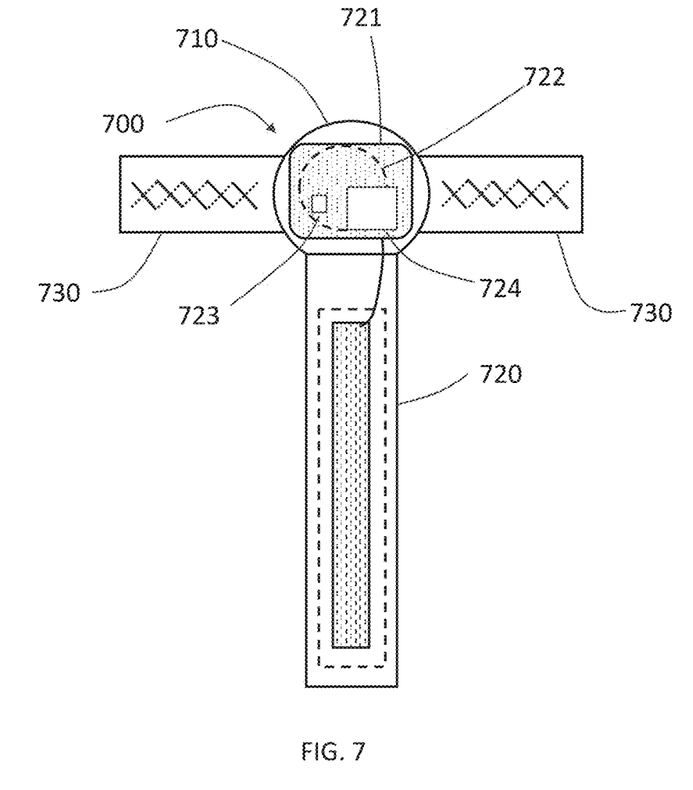
FIG. 7 is a top plan view of a wetness detector integrated with a stretch sensor monitoring breath or belly movement, in accordance with some embodiments of the invention.

FIG. 7 depicts another embodiment of present invention. The T-shape detector system 700 comprises a signal processing unit 710, a wetness sensing element 720, a stretch sensor 730 and/or multiple other sensors but not limited to inertial sensor, vital sign sensor, gas sensor and chemical sensor. A stretch sensor 730 may be attached near wearer's waist or belly. It may monitor wearer's breath period due to the wear's belly movement. In a variation of embodiment, the stretch sensor 730 may be used as a wetness sensing element 720 and attached to a wet prone region on an absorbent article or a garment facing an absorbent article. When an absorbent article is wet, the stretch sensor 730 may be stretched and result in capacitance change.

Having thus described several aspects of at least one embodiment of this invention, it is to be appreciated that various alterations, modifications, and improvements will readily occur to those skilled in the art. Such alterations, modifications, and improvements are intended to be part of this disclosure, and are intended to be within the spirit and scope of the invention. Further, though advantages of the present invention are indicated, it should be appreciated that not every embodiment of the invention will include every described advantage. Some embodiments may not implement any features described as advantageous herein and in some instances. Accordingly, the foregoing description and drawings are by way of example only.

Various aspects of the present invention may be used alone, in combination, or in a variety of arrangements not specifically discussed in the embodiments described in the foregoing, and it is, therefore, not limited in its application to the details and arrangement of components set forth in the foregoing description or illustrated in the drawings. For example, aspects described in one embodiment may be combined in any manner with aspects described in other embodiments.

The invention may be embodied as a method, of which various examples have been described. The acts performed as part of the method may be ordered in any suitable way. Accordingly, embodiments may be constructed in which acts are performed in an order different than illustrated, which may include different (e.g., more or less) acts than those which are described, and/or which may involve performing some acts simultaneously, even though the acts are shown as being performed sequentially in the embodiments specifically described above.

Use of ordinal terms such as "first," "second," "third," etc., in the claims to modify a claim element does not by itself connote any priority, precedence, or order of one claim element over another or the temporal order in which acts of a method are performed, but are used merely as labels to distinguish one claim element having a certain name from another element having the same name (but for use of the ordinal term) to distinguish the claim elements.

Also, the phraseology and terminology used herein is for the purpose of description and should not be regarded as limiting. The use of "including," "comprising," or "having," "containing," "involving," and variations thereof herein, is meant to encompass the items listed thereafter and equivalents thereof as well as additional items.

What is claimed is:

1. An apparatus for sensing presence of liquid in an absorbent article adapted to be worn by a wearer, the absorbent article having a first, inwardly-facing exterior surface and a second, outwardly-facing exterior surface, the first, inwardly-facing exterior surface residing, when the absorbent article is worn by the wearer, closer to the wearer than the second, outwardly-facing exterior surface, the apparatus comprising:
   a plurality of sensing elements for detecting presence of liquid in the absorbent article, each of the plurality of sensing elements being formed at least partially of conductive fabric, polymer, and/or printed conductive ink; and
   at least one adhesive element adapted to adhere the apparatus to (1) the second, outwardly-facing exterior surface of the absorbent article, or (2) to a garment adapted to be worn by the wearer of the absorbent article so that at least part of the apparatus resides between the garment and the second, outwardly-facing exterior surface of the absorbent article;
   wherein, when the apparatus is adhered to the second, outwardly-facing exterior surface of the absorbent article or to the garment, each of the plurality of sensing elements resides proximate a different, corresponding region of the absorbent article, and is configured to separately detect presence of liquid at the corresponding region;
   wherein the apparatus comprises a first non-conductive layer separating the plurality of sensing elements from the at least one adhesive element; and
   wherein the apparatus comprises a conductive shield layer, and a second non-conductive layer separating the plurality of sensing elements from the conductive shield layer.

2. The apparatus of claim 1, wherein at least one of the plurality of sensing elements is configured to detect presence of liquid in the absorbent article based at least in part on a change in capacitance of the absorbent article.

3. The apparatus of claim 1, wherein the plurality of sensing elements are arranged so that the different regions are located on a front, a bottom and/or a back of the absorbent article when the absorbent article is worn by the wearer.

4. The apparatus of claim 1, wherein the plurality of sensing elements are arranged so as to form a strip.

5. The apparatus of claim 4, wherein the strip is constructed, at least in part, by using a conductive filament to attach the plurality of sensing elements to a non-conductive strip-like structure.

6. The apparatus of claim 5, wherein the conductive filament comprises one or more of fabric, metal and polymer.

7. The apparatus of claim 4, wherein the conductive filament attaches the plurality of sensing elements to the non-conductive strip-like structure via sewing and/or winding, in one or more of a mesh, a grid, a rectangular, or a circular shape.

8. The apparatus of claim 4, wherein the conductive filament is produced via 3-D printing.

9. The apparatus of claim 1, wherein being formed at least partially of conductive fabric, polymer, and/or printed conductive ink enables each of the plurality of sensing elements to be stretched, flexed and washed.

10. The apparatus of claim 1, comprising a signal processing unit which is electrically and mechanically connected to the plurality of sensing elements.

11. The apparatus of claim 10, wherein the signal processing unit is configured to transmit information relating to a detected presence of liquid in the absorbent article to at least one external device.

12. The apparatus of claim 10, wherein the signal processing unit is configured to cause information relating to a detected presence of liquid in the absorbent article to be stored in at least one storage repository.

13. The apparatus of claim 1, comprising a first end and a second end which is distal the first end, wherein the apparatus has physical dimensions enabling both the first end and the second end to be adhered to a second exterior surface of an absorbent article adapted to be worn by a baby.

14. The apparatus of claim 1, comprising at least one of: a breathing sensor for sensing respiration by the wearer, an inertial sensor, a temperature sensor, a chemical sensor, and an optical sensor.

15. The apparatus of claim 1, wherein the plurality of sensing elements are arranged so that, when the apparatus is adhered to the second exterior surface of the absorbent article or to the garment, the plurality of sensing elements reside at least 0.5 mm apart.

* * * * *